US00PP12393P2

(12) United States Plant Patent
Zaiger et al.

(10) Patent No.: US PP12,393 P2
(45) Date of Patent: Feb. 5, 2002

(54) NECTARINE TREE NAMED 'HONEY HAVEN'

(76) Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 0 days.

(21) Appl. No.: 09/824,444

(22) Filed: Apr. 3, 2001

(51) Int. Cl.[7] ..... A01H 5/00
(52) U.S. Cl. ..... Plt./190
(58) Field of Search ..... Plt./190

*Primary Examiner*—Bruce R. Campell
*Assistant Examiner*—Anne Marie Grünberg

(57) ABSTRACT

A new and distinct variety of nectarine tree (*Prunus persica* var. *nucipersica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices such as pruning, thinning, spraying, irrigation and fertilization. Its novelty consists of the following unique combination of features that are desirable in a new variety:

1. Regular and heavy production of fruit.
2. Vigorous and upright growth.
3. Fruit having an attractive red skin color.
4. Early maturity of large size fruit.
5. Fruit with firm flesh, very good flavor and eating quality.
6. The fruit having good handling and shipping quality.

1 Drawing Sheet

FIELD OF INVENTION

In the field of plant genetics, we conduct an extensive and continuing plant-breeding program including the organization and asexual reproduction of orchard trees, of which plums, peaches, nectarines, apricots, cherries and interspecifics are exemplary. It was against this background of our activities that the present variety of nectarine tree was originated and asexually reproduced by us in our experimental orchard located near Modesto, Stanislaus County, Calif.

PRIOR VARIETIES

Among the existing varieties of nectarine and peach trees which are known to us, and mentioned herein, 'May Grand' Nectarine (U.S. Plant Pat. No. 2,794), 'Early Sungrand' Nectarine (U.S. Plant Pat. No. 1,420) and 'Royal Gold' Peach (U.S. Plant Pat. No. 2,663).

ORIGIN OF THE VARIETY

The present new and distinct variety of nectarine tree (*Prunus persica* var. *nucipersica*) was originated by us in our experimental orchard located near Modesto, Calif. as a seedling from an open pollinated selection of a cross between two selected seedlings with field identification numbers 36EB64 and 9GC175. The maternal parent (36EB64) originated from an open pollinated seedling selection which originated as a second-generation seedling of a cross between 'May Grand' Nectarine (U.S. Plant Pat. No. 2,794) and a peach of unknown parentage. The paternal parent (9GC175) originated from a second-generation seedling of a cross between an open pollinated seedling of 'Early Sungrand' Nectarine (U.S. Plant Pat. No. 1,420) and 'Royal Gold' Peach (U.S. Plant Pat. No. 2,663). A large group of these seedlings growing on their own root were planted and maintained under close observation by us, during which time we recognized the desirable fruit characteristics of one seedling, which is the present variety, and selected it in 1994 for asexual propagation and commercialization.

ASEXUAL REPRODUCTION OF THE VARIETY

Asexual reproduction of the new and distinct variety of nectarine tree was by budding to 'Nemaguard Rootstock' (non-patented), the standard rootstock for nectarines in California, as performed by us in our experimental orchard located near Modesto, Calif., and shows that reproductions run true to the original tree and all characteristics of the tree and its fruit are established and transmitted through succeeding asexual propagations.

SUMMARY OF THE VARIETY

A new and distinct variety of nectarine tree which is of large size, vigorous upright growth, and a productive and regular bearer of large size, yellow flesh, clingstone fruit with very good flavor and eating quality. The fruit is further characterized by having a high degree of attractive red skin color, firm flesh, with good handling and shipping quality. The fruit of the present new variety, when compared to 'May Grand' Nectarine (U.S. Plant Pat. No. 2,794), has a higher degree of attractive red skin color, is less susceptible to split stones, the flesh has a mild, sweet, sub-acidic flavor compared to the regular acidic flavor and is approximately 3 days earlier in maturity.

PHOTOGRAPH OF THE VARIETY

The accompanying color photographic illustration shows typical specimens of the foliage and fruit of the present new nectarine variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is detailed botanical description of the new variety of nectarine tree, its flowers, foliage and fruit, as based on observations of 6 year old specimens growing on 'Nemaguard' Rootstock (non-patented), grown near Modesto, Calif., with color terminology (except those in common terms) in accordance with Reinhold Color Atlas by A. Kornerup and J. H. Wanscher.

Tree:

*Size.*—Large. Tree height controlled by selective pruning to 10 to 12 feet in height and 10 to 12 feet in width for economical harvesting of fruit.

*Vigor.*—Vigorous. Grows 6 to 7 feet in height the first growing season. During the first dormant season it is pruned to 4 to 5 feet in height and primary scaffolds are selected.

*Form.*—Usually pruned to vase shape.

*Branching habit.*—Upright. Crotch angle approximately 35 degrees.

*Productivity.*—Productive. Normal fruit set is 1½ to more times the amount of desired fruit. Fruit is reduced and spaced by thinning to produce marketable fruit size.

*Bearer.*—Regular. Has set heavy crop for 5 consecutive years. No alternate bearing observed.

*Density.*—Medium dense. Pruning to vase shape by removing some of the center branches to allow for more sunlight penetration.

*Hardiness.*—Tree grown in USDA Hardiness Zone 9. Winter chilling requirement is approximately 800 hours below 45° F. Hardy in all stone fruit growing areas of California.

Trunk:

*Size.*—Large. Average circumference of 22½ inches at 14 inches above ground on 6 year old trees. Varies with soil type, climatic conditions and cultural practices.

*Texture.*—Medium shaggy, becoming rougher with age.

*Color.*—Brown to tobacco brown (5E-4) to (5-F-6).

Branches:

*Size.*—Medium. Circumference averages 9 inches at 38 inches above ground.

*Surface texture.*—Smooth to medium rough. Roughness increases with age of branch.

*Lenticels.*—Average number of 16 in a 4 square inch surface. Small to medium in size. Average of 5/32 inch in length. Average of 1/16 inch in width. Size increases as branches become larger. Color varies from brownish orange to brownish yellow (5-C-6) to (5-C-8). Varies with age of growth.

*Color.*—First years new growth varies from lettuce green (30-D-7) to light brown (5-B-6). Older more mature growth from oak brown to yellowish brown (5-D-6) to (5-E-8). Color becomes darker with age of branch.

Leaves:

*Size.*—Large. Average length 5 inches. Average width 1 15/32 inch.

*Form.*—Lanceolate.

*Apex.*—Acuminate.

*Base.*—Cuneate.

*Margin.*—Serrate.

*Thickness.*—Medium.

*Surface.*—Varies from relatively smooth to undulated. Upper surface relatively smooth, slight indentation over midrib and veining. Lower surface relatively smooth, small ridges created by midrib and pinnate venation. Both surfaces are glabrous.

*Petiole.*—Medium. Average length 23/64 inch. Average width 1/16 inch. Grooved longitudinally. Color varies from pea green to grayish green (29-D-5) to (29-D-6).

*Glands.*—Reniform. Medium in size. Average diameter 3/64 inch. Number varies from 2 to 3, average number 2. Color — reddish brown (9E-5). Located on the base of the leaf blade and the upper portion of the petiole.

*Color.*—Upper surface — green to dark green (29-F-6) to (29-F-8). Lower surface — grayish green to green (29-E-4) to (29-E-6).

Flower buds:

*Size.*—Large. Average length 5/8 inch. Average diameter 27/64 inch three days before bloom.

*Form.*—Conical, plump, free, becoming elongated at maturity.

*Color.*—Pale pink to pastel pink (11-A-3) to (11-A-4).

*Hardiness.*—Hardy in all stone fruit growing areas of California.

*Pubescence.*—Pubescent on outer surface of sepals.

Flowers:

*Size.*—Large, showy. Average height 11/16 inch. Average diameter 1 9/16 inch.

*Petals.*—Number — 5, alternately arranged to sepals. Ovate, edges vary from smooth to slightly scalloped. Narrows at point of attachment. Average length ¾ inch. Average width 21/32 inch. Color — pink to pastel pink (11-A-3) to (11-A-4). Color fades with age of flower.

*Sepals.*—Number — 5. Alternately arranged to petals. Average length 11/64 inch. Average width 5/32 inch. Color of lower surface varies from ruby to grayish ruby (12-D-6) to (12-D-8), pubescent. Upper surface varies from patina green (28-C-5) in the center to a narrow margin of grayish ruby (12-D-6) on the outer edges, glabrous.

*Stamens.*—Number of stamens varies from 40 to 49. Average number 46. Average length 9/16 inch. Filament color — white (1-A-1), turning pink with age of bloom. Anther color — red (11-A-6).

*Pollen.*—Present, self-fertile. Color — light yellow to maize yellow (3-A-4) to (3-A-6).

*Pistil.*—Normally one. Varies from 1 to 2. Average length ½ inch. Color — yellowish white to pale yellow (1-A-2) to (1-A-3). Stigma height slightly above anthers, 1/16 inch. Pubescence — wanting.

*Aroma.*—Slight.

*Pedicel.*—Average length 3/16 inch. Average width 1/16 inch. Color — apple green (29-C-7).

*Blooming period.*—Date of First Bloom Feb. 24, 2000. Date of Petal Fall Mar. 6, 2000. Varies slightly with climatic conditions.

*Color.*—Light pink to pink (13-A-3) to (13-A-4).

Fruit:

*Maturity when described.*—Shipping ripe.

*Date of first picking.*—Jun. 15, 2000.

*Date of last picking.*—Jun. 22, 2000. Varies slightly with climatic conditions.

*Size.*—Average diameter axially 2⅜ inches to 2½ inches. Average transversely in suture plane 2½ inches to 2⅝ inches. Average weight 195.96 grams. Average weight varies slightly with fertility of the soil, amount of thinning and climatic conditions.

*Form.*—Globose, nearly symmetrical, slightly elongated.

*Suture.*—Shallow, extends from base to apex.

*Ventral surface.*—Usually rounded, some fruit slightly lipped.

*Apex.*—Usually rounded, varies from slight tip to slight depression.

*Base.*—Retuse.

*Cavity.*—Slightly elongated in suture plane. Average depth 5/16 inch. Average breadth ½ inch.

Stem:

*Size.*—Average length 5/16 inch. Average diameter 5/32 inch. Enlarged at point of attachment to fruit.

*Color.*—Grayish yellow to olive brown (4-C-5) to (4-D-5).

Flesh:

*Ripens.*—Evenly.

*Texture.*—Firm, meaty.

*Fibers.*—Few, small and tender.

*Firmness.*—Firm, good handling and shipping quality.

*Aroma.*—Slight.

*Amydgalin.*—Undetected.

*Eating quality.*—Very good.

*Flavor.*—Very good, good balance between acid and sugar.

*Juice.*—Moderate, enhances flavor.

*Brix.*—Average 10.5°.

*Color.*—Yellow to butter yellow (4-A-4) to (4-A-5). Pit cavity butter yellow to banana yellow (4-A-5) to (4-B-5), non-bleeding, except for very slight reddish yellow staining near apex.

Skin:

*Thickness.*—Medium, shows minimal bruising or scarring with picking and packing trials.

*Texture.*—Medium. Tenacious to the flesh.

*Down.*—Wanting.

*Tendency to crack.*—None.

*Color.*—Yellow ground color (3-B-6) to (3-B-7), overspread with red to deep red (10-C-8) to (10-E-8).

Stone:

*Type.*—Clingstone.

*Size.*—Large. Average length 1½ inches. Average width 1 5/32 inches. Average thickness 13/16 inches.

*Form.*—Oval to ovoid, varies slightly with some stones.

*Base.*—Usually straight, varies from straight to rounded.

*Apex.*—Cuspidate.

*Surface.*—Irregularly furrowed toward apex, pitted toward base. Pit cavities vary from rounded to elongated in shape. Small ridges with a rough, irregular surface.

*Sides.*—Equal to unequal. Some stones have one side slightly larger, extending farther from the suture plane.

*Tendency to split.*—Very slight.

*Color.*—Brownish yellow to light brown (6-C-8) to (6-D-8) when dry.

Use: Dessert. Market — local and long distance.

Keeping quality: Good, fruit holds firm for two weeks in cold storage at 38 to 42° F. with no internal breakdown of flesh or appreciable loss of eating quality.

Shipping quality: Good, picking and packing of fruit gave minimal bruishing or scarring of flesh or skin.

Disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of nectarine tree substantially as illustrated and described, which is of large size, vigorous upright growth and a productive and regular bearer of large size, clingstone fruit with firm flesh, very good flavor and eating quality; the fruit is further characterized by its attractive red skin color, good handling and shipping quality; and when compared to 'May Grand' Nectarine (U.S. Plant Pat. No. 2,794) the fruit of the new variety has a higher degree of attractive red skin color, less susceptible to split stones, is sub-acidic instead of acidic and matures approximately 3 days earlier.

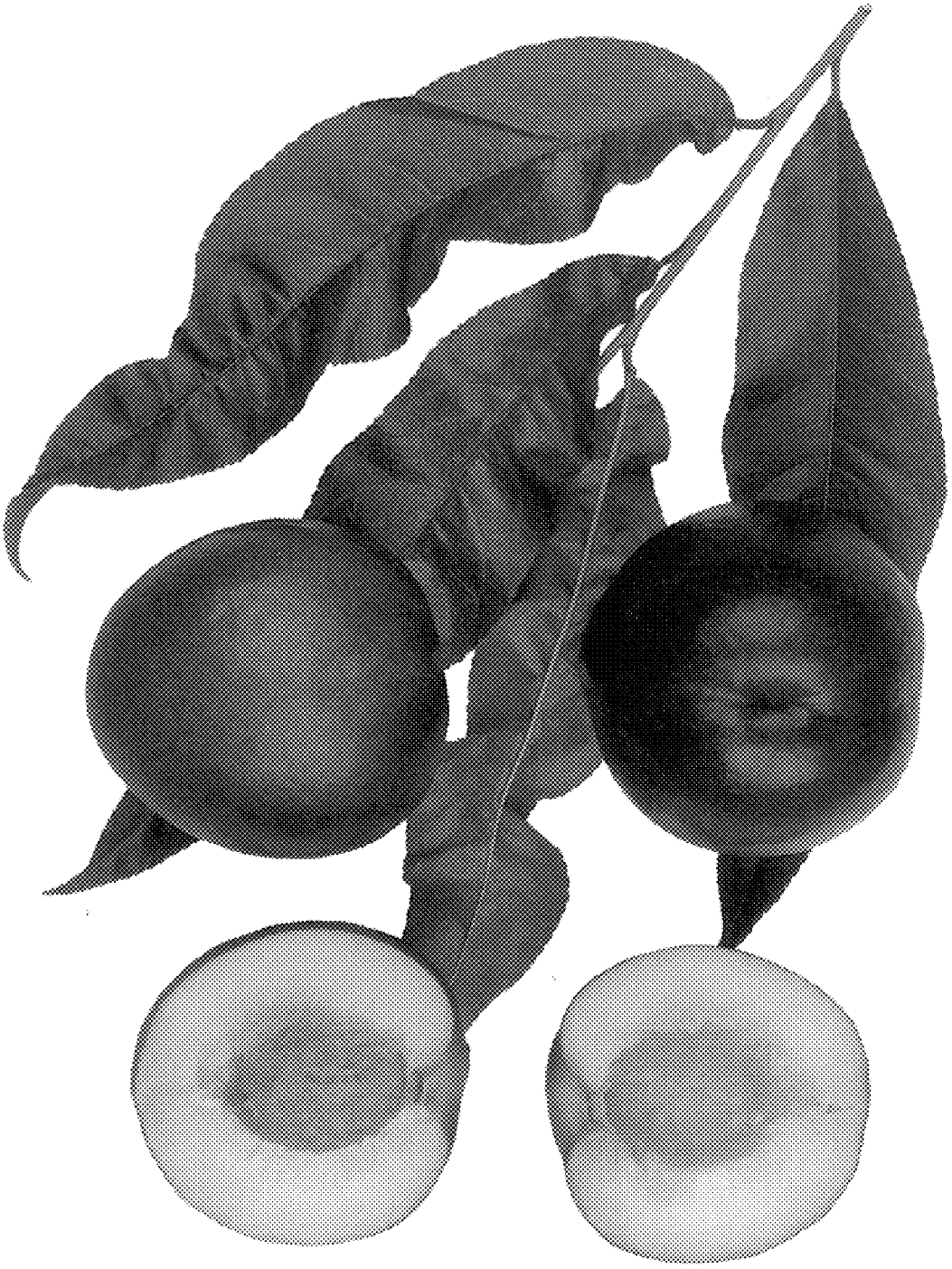

* * * * *